(12) United States Patent
Duckett, III

(10) Patent No.: US 12,402,786 B2
(45) Date of Patent: Sep. 2, 2025

(54) HYPERSPECTRAL/MULTISPECTRAL IMAGING SYSTEM WITH SIMULTANEOUS WHITE LIGHT IMAGING

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 77 days.

(21) Appl. No.: 18/431,404

(22) Filed: Feb. 2, 2024

(65) Prior Publication Data

US 2025/0213102 A1 Jul. 3, 2025

Related U.S. Application Data

(60) Provisional application No. 63/615,986, filed on Dec. 29, 2023.

(51) Int. Cl.
*A61B 1/06* (2006.01)
*A61B 1/00* (2006.01)
(Continued)

(52) U.S. Cl.
CPC ........ *A61B 1/0638* (2013.01); *A61B 1/00009* (2013.01); *A61B 1/04* (2013.01);
(Continued)

(58) Field of Classification Search
CPC ..... A61B 1/0638; A61B 1/00009; A61B 1/04; H04N 7/0806; H04N 7/183; H04N 23/555; H04N 23/74
See application file for complete search history.

(56) References Cited

U.S. PATENT DOCUMENTS

2015/0238126 A1* 8/2015 Saito .................... A61B 5/1459
600/339
2018/0020965 A1* 1/2018 Kang ................... A61B 1/0638
600/473
(Continued)

FOREIGN PATENT DOCUMENTS

WO 2022211820 A1 10/2022
WO 2023094351 A1 6/2023

OTHER PUBLICATIONS

Rodriquez, K., International Search Report and Opinion, Jan. 22, 2025, pp. 1-8, International Search Bureau, USA.

*Primary Examiner* — Nasim N Nirjhar
(74) *Attorney, Agent, or Firm* — David N. Villalpando; Jacqueline Cohen

(57) ABSTRACT

A hyperspectral imaging method and system including cameras with simultaneous white light imaging capability are presented. A video system includes a camera and a light source adapted to provide white light illumination at a first frame rate suitable for live video, and to provide intermittent narrowband illumination for individual frames interspersed among the white light illuminated frames, where the spectrum of the narrowband illumination varies amongst the interspersed frames permitting a series of at least two differently illuminated narrowband interspersed frames to be assembled into a multispectral or hyperspectral data cube at a second frame rate. The system also includes a processor adapted to receive an image signal and create a live video feed based on the white light illuminated frames by replacing the narrowband illuminated frames with generated or previously collected frames.

20 Claims, 6 Drawing Sheets

(51) Int. Cl.
  *A61B 1/04* (2006.01)
  *H04N 7/08* (2006.01)
  *H04N 7/18* (2006.01)
  *H04N 23/50* (2023.01)
  *H04N 23/74* (2023.01)

(52) U.S. Cl.
  CPC ........... *H04N 7/0806* (2013.01); *H04N 7/183* (2013.01); *H04N 23/555* (2023.01); *H04N 23/74* (2023.01)

(56) References Cited

U.S. PATENT DOCUMENTS

| | | | |
|---|---|---|---|
| 2022/0225865 A1* | 7/2022 | Saito | A61B 1/044 |
| 2022/0257101 A1* | 8/2022 | Fei | A61B 1/0607 |
| 2023/0077690 A1 | 3/2023 | Tsutaoka | |
| 2024/0210310 A1* | 6/2024 | Cutrale | A61B 1/0623 |

* cited by examiner

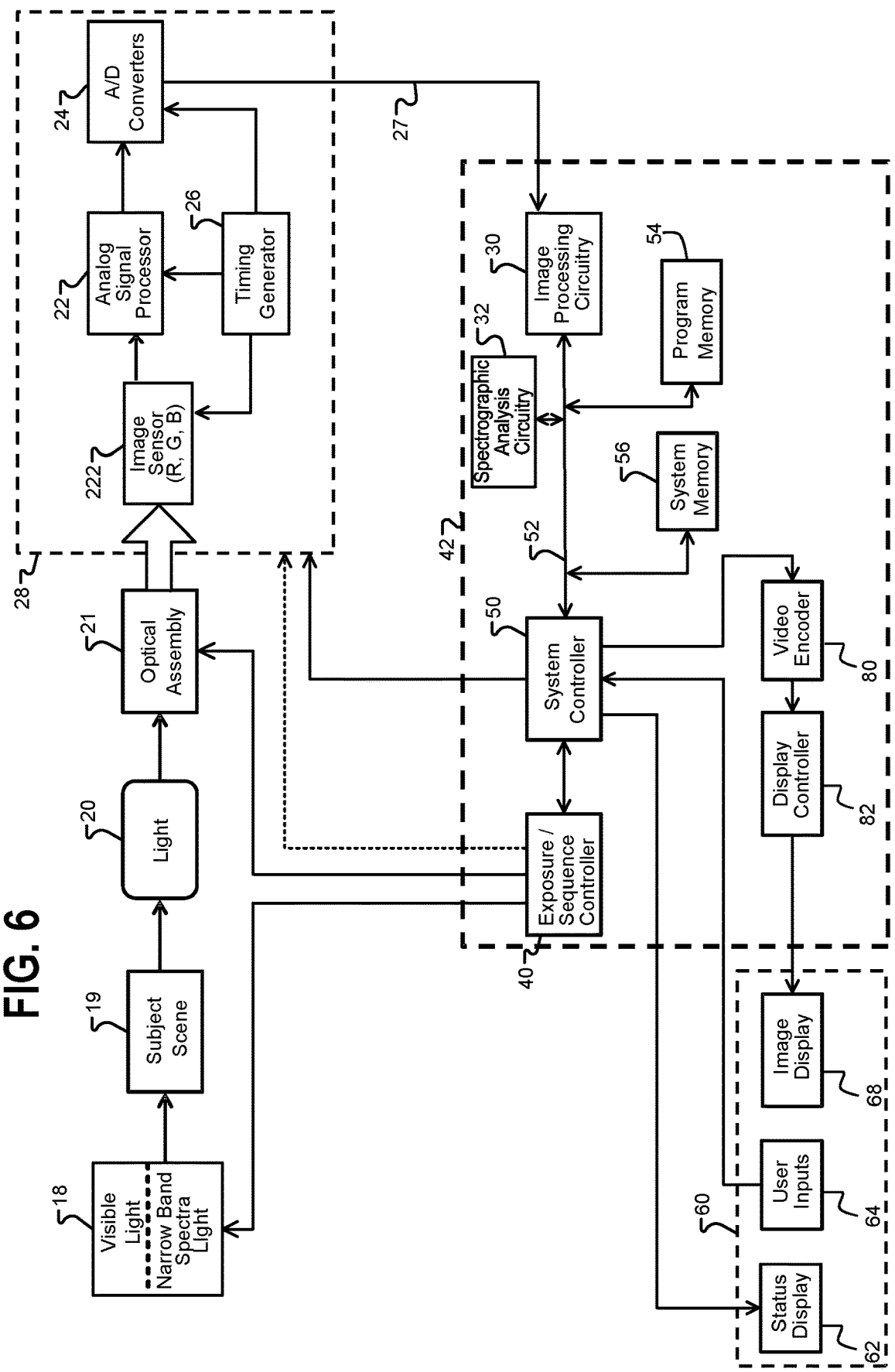

HYPERSPECTRAL/MULTISPECTRAL IMAGING SYSTEM WITH SIMULTANEOUS WHITE LIGHT IMAGING

TECHNICAL FIELD

This disclosure relates to multispectral imaging (MSI) or hyperspectral imaging (HSI) systems.

BACKGROUND

FIG. 1 illustrates an endoscopic imaging system with an endoscopic illuminator according to the prior art. An endoscope 101 includes an endoscopic shaft member 102 attached to a handle or camera head 103. Illumination source 104 ("light source 104") may be integrated as depicted within a scope controller 108, which also powers and communicates with endoscope 101 through cable 107. Scope controller 108 provides an image signal to a display 109. Light collected by an objective lens at the distal end of the endoscopic shaft 102 is alternatively captured by an image sensor within the shaft or relayed down the length of the shaft via a relay lens system to an image sensor located within the camera head. The distal end of the shaft 102 is inserted into an otherwise inaccessible space, such as body cavity accessed through a small incision. Light source 104 produces illumination light that is directed into a light guide 105 which carries the illumination light to a light post 106, where the light guide is coupled with another light guide (such as a fiber bundle) that carries the illumination to the distal end of the shaft 102, where it is then able to illuminate a scene within the inaccessible space. As an alternate to utilizing an imaging endoscope 101 to provide illumination, an endoscopic light source might simply embody a light pipe comprising a shaft which may be inserted through a separate incision from that of an imaging endoscope.

Classical video endoscopes are used for color video imaging of an examination area inside the body. Multispectral or hyperspectral imaging can provide users of endoscopes with additional information that can be used during operations or diagnostics. For example, in medical technology, physiological imaging with multispectral or hyperspectral methods may be used to analyze physiological parameters such as hemoglobin content and the oxygenation of hemoglobin in the examination area, which are displayed spatially resolved by false colors. Multispectral and hyperspectral imaging also have a variety of further applications both in and outside the medical field.

To integrate multispectral or hyperspectral imaging capability with a medical scope typically requires an imaging spectrometer construction that is small in size and, depending on the application, inexpensive as compared to typical imaging spectrometers for other applications.

BRIEF DESCRIPTION OF THE INVENTION

It is an object of the invention to provide hyperspectral imaging methods, devices and cameras with simultaneous white light imaging capability. It is a further object of the invention to provide improved adaptability to desired applications. It is a further object of the invention to provide such devices spectral acquisition that is configurable for use with a variety of image sensors. It is a further object of the invention to provide such devices that can operate across a desired range while being sized to fit in the form factor for a medical scope camera.

According to a first aspect of the invention, an endoscopic video system includes a light source adapted to provide white light illumination at a first frame rate suitable for live video, and to interrupt the white light illumination and provide narrowband illumination for individual frames interspersed among the white light illuminated frames at regular or irregular intervals, wherein the spectrum of the narrowband illumination varies amongst the interspersed frames sufficient for a series of at least two differently illuminated narrowband interspersed frames to be assembled into a multispectral or hyperspectral data cube at a second frame rate. The system includes a processor adapted to receive an image signal based on sensor data received from a focal plane array sensor and create a live video feed based on the white light illuminated frames by replacing the narrowband illuminated frames with frames generated from one or more time-adjacent white light illuminated frames, and to generate the multispectral or hyperspectral data cube at a second frame rate based on the narrowband illuminated frames.

According to some implementations of the first aspect, the majority of frames are illuminated by white light. For example, at least 90% of the frames may be illuminated by white light.

According to some implementations of the first aspect, at least some of the narrowband spectra overlap with portions of the white light illumination spectrum.

According to some implementations of the first aspect, the number of different narrowband spectra used for illuminating the interspersed frames is greater than 10. The number of different narrowband spectra used for illuminating the interspersed frames may be greater than 50.

According to some implementations of the first aspect, the processor is further adapted to generate an image from information contained in the hyperspectral or multispectral data cube and cause the image to be displayed in a separate display area than a display area showing the video feed. Such an image generated from the hyperspectral data cube may indicate the oxygenation, tissue water index, or perfusion of tissue in an image scene.

According to some implementations of the first aspect, the spectral bandwidth of the narrowband illumination spectra is about 5 nm.

According to some implementations of the first aspect, the spectral bandwidth of the narrowband illumination spectra is about 10 nm.

According to some implementations of the first aspect, the spectral bandwidth of the narrowband illumination spectra is about 25 nm.

According to some implementations of the first aspect, the white light illumination and the narrowband illumination have total power that is similar sufficient such that exposure characteristics of the sensor do not have to be different for the frames illuminated with narrowband illumination than it is for the frames illuminated by white light in order to acquire data for the multispectral or hyperspectral data cube.

According to some implementations of the first aspect, data from multiple narrowband illuminated frames of identical narrowband illumination are averaged to generate a data cube and/or a slice of a data cube.

According to a second aspect of the invention, a method is provided including causing a light source for a medical scope to provide white light illumination for frames at a first frame rate suitable for live video, and causing the light source to interrupt the white light illumination and provide narrowband illumination for individual frames interspersed among the white light illuminated frames at regular or irregular intervals, wherein the narrowband spectrum varies amongst the interspersed frames sufficient for a series of at least two differently illuminated narrowband interspersed frames to be assembled into a multispectral or hyperspectral data cube at a second frame rate. The method includes imaging the white light illuminated fames and narrowband illuminated frames onto a focal plane array image sensor at the medical scope. The method includes, at a processor, receiving an image signal based on sensor data received from the focal plane array sensor and creating a live video feed based on the white light illuminated frames by replacing the narrowband illuminated frames with frames generated from one or more time-adjacent white light illuminated frames, and generating a multispectral or hyperspectral data cube at a second frame rate based on the narrowband illuminated frames.

In some implementations of the second aspect, the method includes generating an image from information contained in the hyperspectral or multispectral data cube and displaying said image on a separate display area than the live video feed. The image generated from the hyperspectral data cube may indicate the oxygenation, tissue water index, or perfusion of tissue in an image scene.

In some implementations of the second aspect, the spectral bandwidth of the narrowband illumination spectra is about 5 nm.

In some implementations of the second aspect, the spectral bandwidth of the narrowband illumination spectra is about 10 nm.

In some implementations of the second aspect, the spectral bandwidth of the narrowband illumination spectra is about 25 nm.

In some implementations of the second aspect, the white light illumination and the narrowband illumination have total power that is similar sufficient such that exposure characteristics of the sensor do not have to be different for the frames illuminated with narrowband illumination than it is for the frames illuminated by white light in order to acquire data for the multispectral or hyperspectral data cube.

These and other features of the invention will be apparent from the following description of the preferred embodiments, considered along with the accompanying drawings.

BRIEF DESCRIPTION OF THE DRAWINGS

The invention is further explained by the following exemplary descriptions of particular embodiments.

FIG. 6 is a hardware block diagram of system including an example image capture device and light source according to an example embodiment of the invention.

DETAILED DESCRIPTION OF THE VARIOUS EMBODIMENTS

Figure 2:
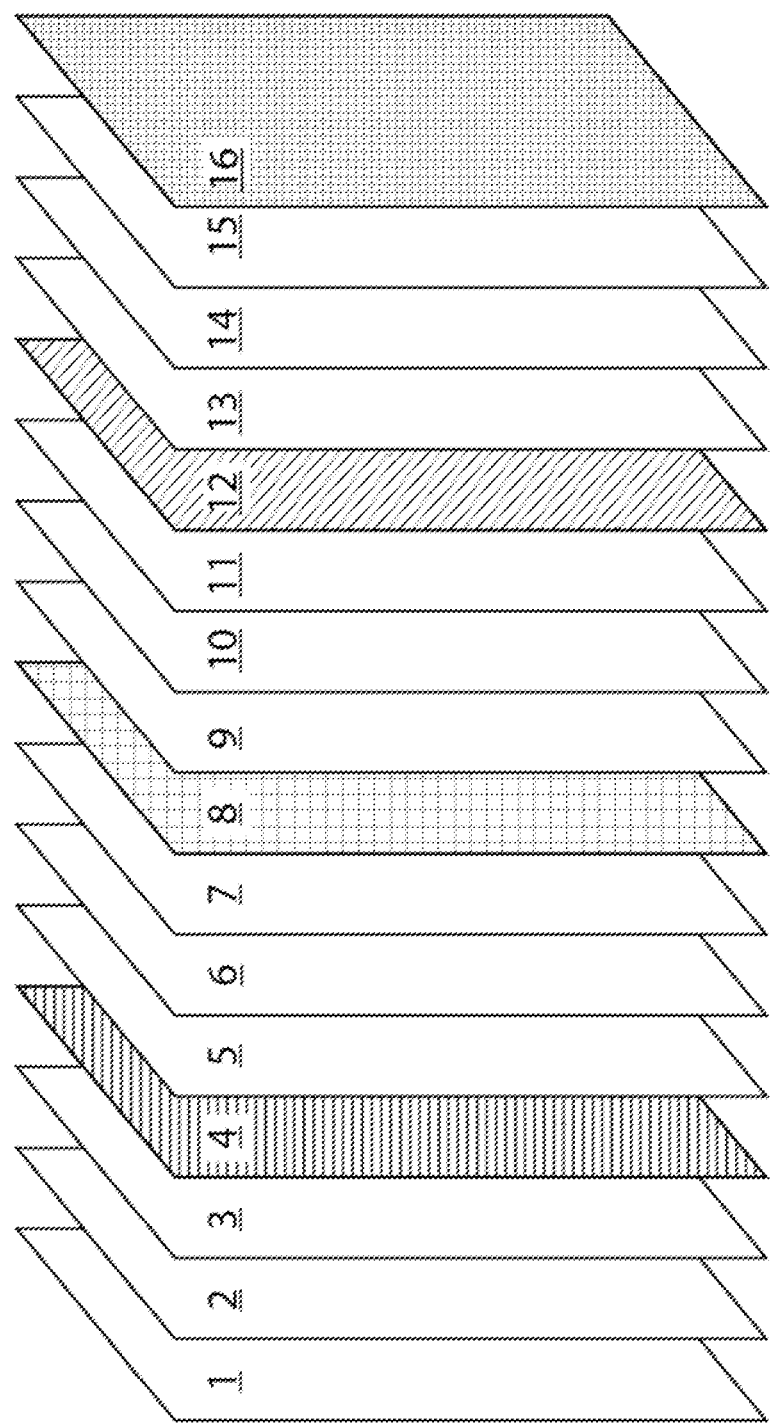
FIG. 2 is a diagram illustrating a series of frames illuminated with narrowband spectrum illuminated frames interspersed among white light illumination frames according to some embodiments.

FIG. 2 is a diagram illustrating a series of frames 1-16 illuminated with narrowband spectrum illuminated frames interspersed among broad-band, white light illuminated frames in a medical imaging system according to some embodiments. The diagram represents a small fraction of time in a longer stream of frames illuminated and acquired to provide both video and spectrographic imagery. The frames are numbered in time order according to a frame rate at which they are illuminated by a light source and acquired by an image sensor. The light source, for example light source 18 (FIG. 6), is controlled to illuminate frames with white light or a one of a plurality of designated narrowband spectra in a sequence, as further described below. As labelled, the white light illuminated frames are interspersed with narrowband illuminated frames labelled frames 4, 8, 12, and 16, which represent a series of narrowband illuminated frames referred to as "narrow spectrum frame #1", "narrow spectrum frame #2", "narrow spectrum frame #3", and "narrow spectrum frame #4". The resulting image stream is used to produce a white light video stream which may be monitored by a user, as described below, and to generate a multispectral or hyperspectral data cube that can be used to perform spectral imaging analysis.

Figure 3:
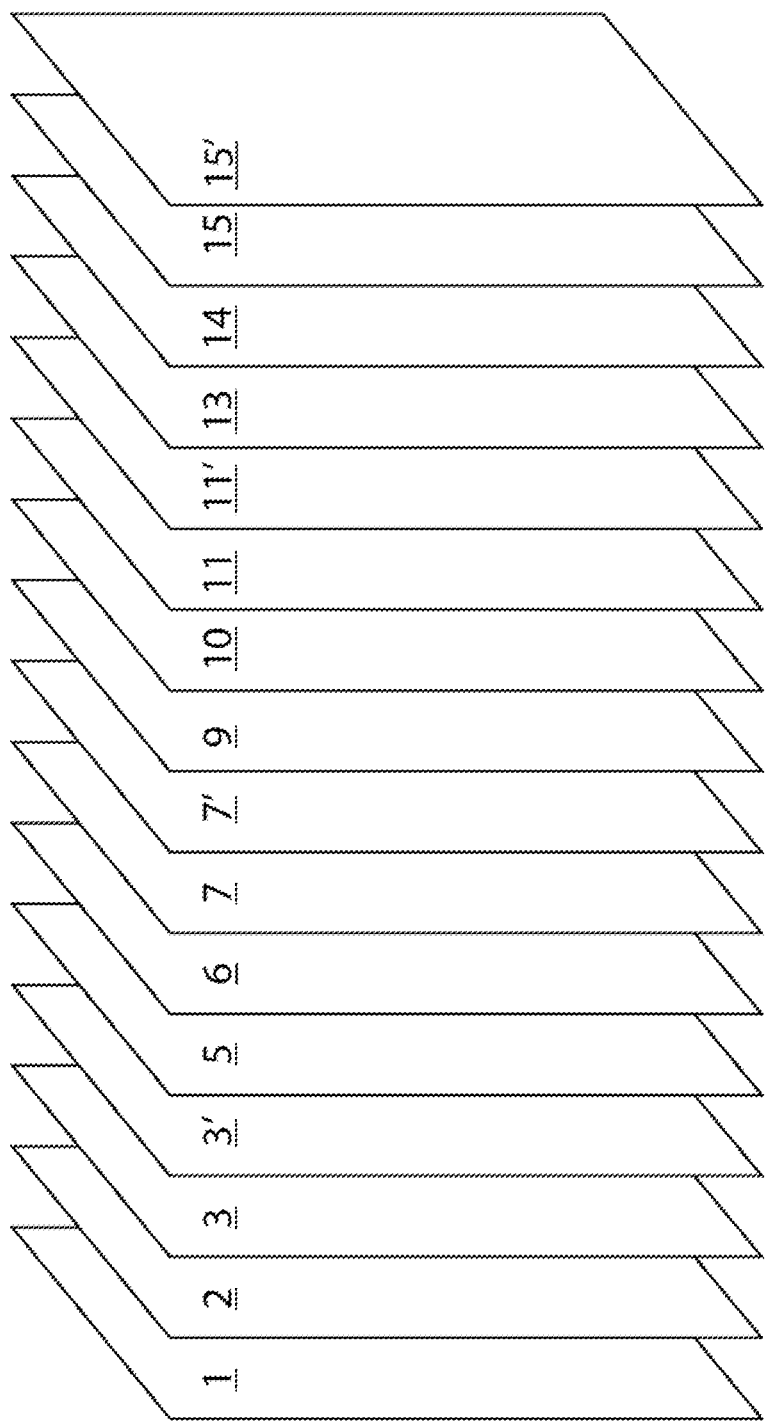
FIG. 3 is a diagram illustrating the series of frames in FIG. 2 with repeated or interpolated frames replacing the narrowband spectrum illuminated frames.

FIG. 3 is a diagram illustrating the series of frames collected in FIG. 2 manipulated to create a video stream which may be monitored by a user, where the collection of HSI/MSI imagery is minimally disruptive to the user. Repeated or interpolated white light frames replace the narrowband spectrum illuminated frames. Referring to FIG. 2 and FIG. 3, to form a white light video stream, the original frames 4, 8, 12, and 16 are replaced with repeated or interpolated frames 3', 7', 11', and 15' in order to produce a continuous and smooth white light video display. Data from frames 4, 8, 12, and 16 is used to produce the multispectral or hyperspectral data cube for spectral analysis and spectral imaging, as further described below. These MSI/HSI frames are, in preferred embodiments, not displayed to the user as part of the video stream.

Figure 4:
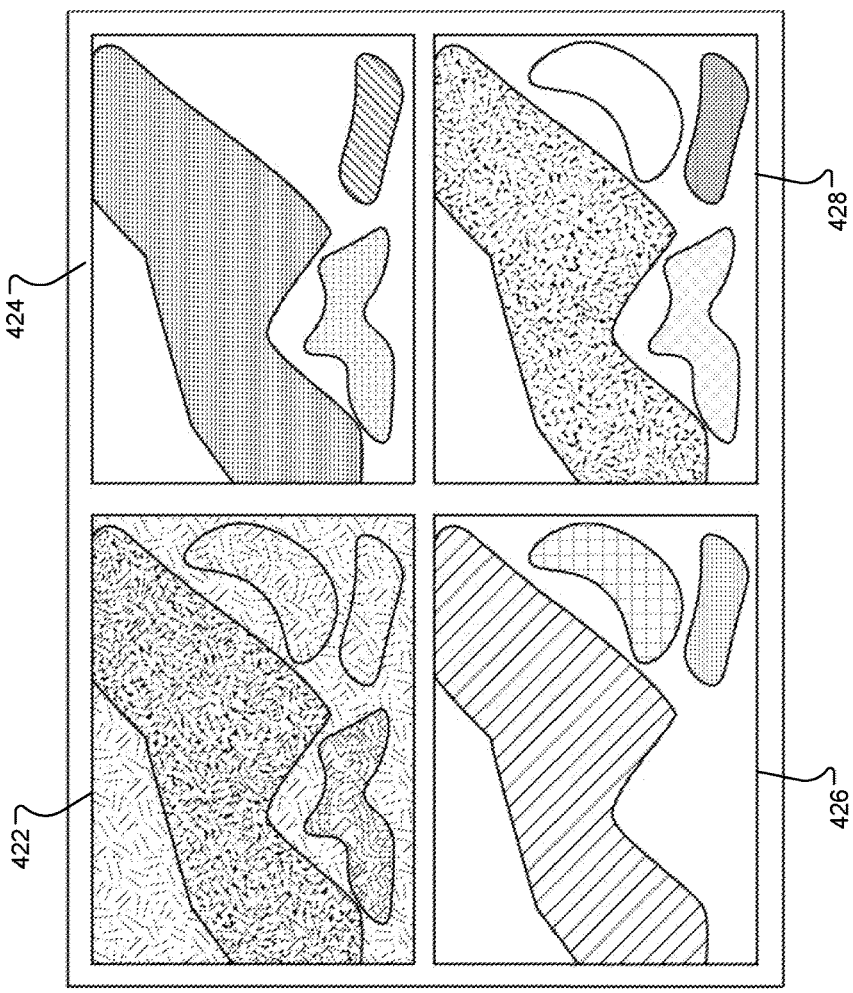
FIG. 4 is a diagram illustrating a hyperspectral data cube based on the narrowband spectrum illuminated frames used to generate spectral imaging for display.
Figure 4:
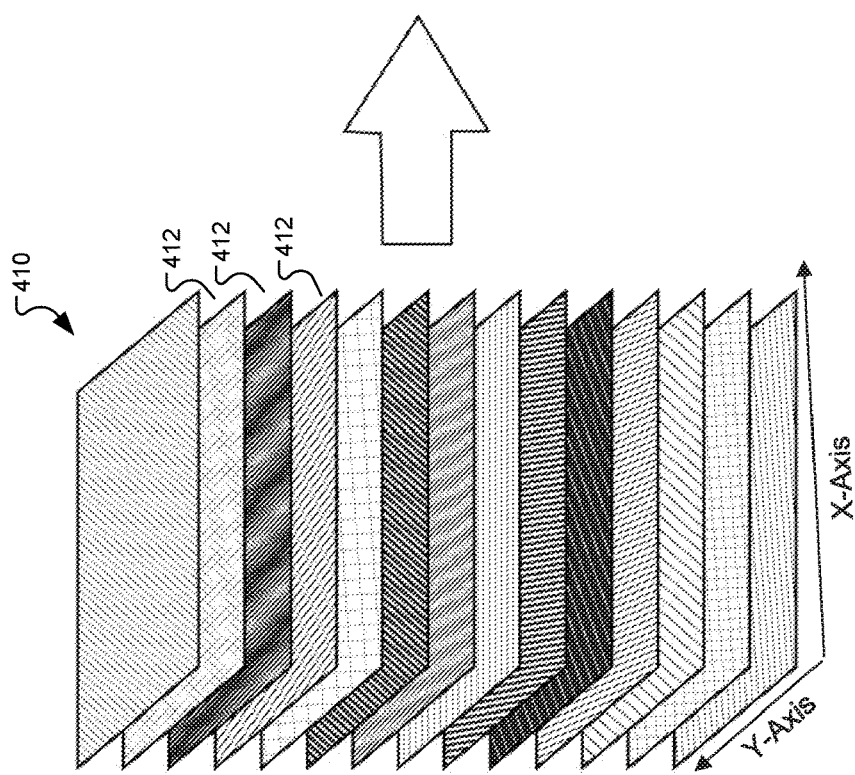

FIG. 4 is a diagram illustrating a hyperspectral data cube 410 created by the data from the narrowband image frames. This spectral image data may also be displayed in various formats to the user along with live, white light video. Hyperspectral data cube 410 is illustrated with a number of layers 412 each holding data representing spectral intensity of a subject scene for a designated spectrum of narrowband illumination light. Each layer represents an intensity level or grayscale image as acquired from an image sensor with the labelled X-axis and Y-axis representing the two axes of the focal plane array image sensor. The particular number of layers 412 will vary with the number of narrowband illumination spectra used to acquire different narrowband illuminated frames. As illustrated in the exemplary display configuration shown in FIG. 4, the systems and methods as described herein provide a real-time white light video feed 422, and three additional image feeds are shown representing different spectral data showing oxygenation (424), a tissue water index (426) representing tissue water concentration, and a near-infrared (NIR) perfusion index (428) representing perfusion within the tissue in an image scene. The three spectral image feeds 424, 426, and 428 are provided at a lower frame rate than white light video feed 422, as further described below. While these three spectral image feeds are provided in this implementation, spectral analysis of various kinds may be performed in various embodiments based on the spectral data acquired as described herein. Additionally or alternatively, only the live video may be displayed, and the spectral content may be stored in a system memory to be retrieved and analyzed at a later time, or may be used to provide other information to the user of the system, for example, to alert the user to an anomaly that is not readily apparent in the white light video stream but is discernable with the MSI/HSI data. A trained AI, for example, may analyze the frames of the MSI/HSI data on the fly and determine that the user should be alerted to the presence of an anomaly.

Figure 5:
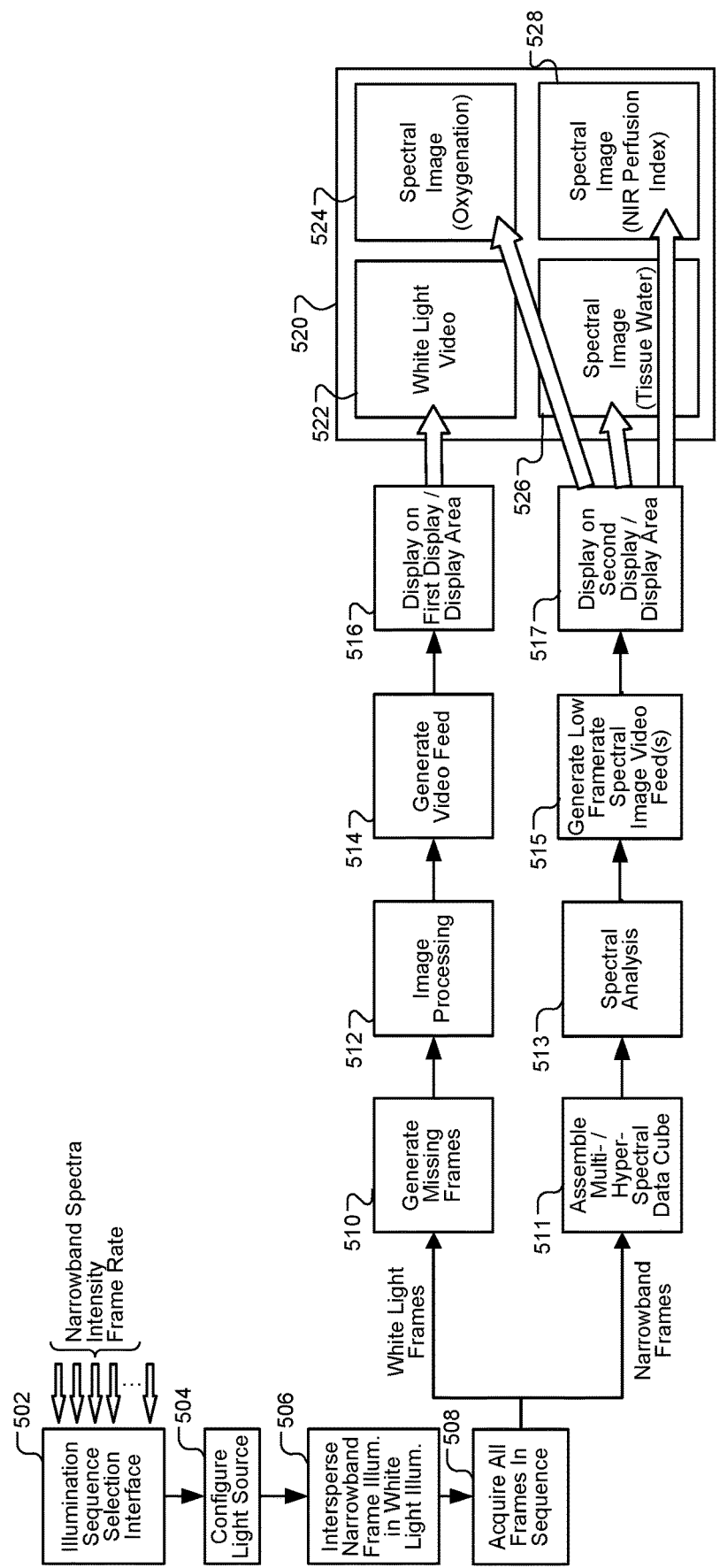
FIG. 5 is a diagram illustrating a process for operating an imaging scope and light source according to some embodiments.

FIG. 5 is a diagram illustrating a process for operating an imaging scope and light source according to some embodiments. The illustrated process is suitable for implementing the frame illumination, acquisition, and analysis discussed above, and is suitable for use with the imaging scope system described herein and variations thereof, performed under control of a processor such as CCU 42 (FIG. 6).

The process starts at block 502 with a user or system selecting an illumination sequence through a selection interface for controlling both light source 18 and CCU 42 for a desired type of spectral analysis. In some embodiments, only one illumination sequence may be available, and no selection is required. In some embodiments, a number of pre-configured profiles are available to specify the combination and sequence of the multiple narrowband spectra used to illuminate the narrowband interspersed frames. An illumination sequence includes information specifying the number and timing of narrowband illuminated frames with respect to the white light illuminated frames, and an identification of the spectral center for the spectra of the narrowband illuminated frames. In this embodiment, the interface allows selection of the narrowband spectra, the illumination intensity at each of the selected spectra, and the frame rate of each of the narrowband spectra. The selection is made through a user interface or by the medical device automatically, either by selecting a stored illumination sequence and profile, or by selecting the number and characteristics of the narrowband spectra individually.

The selection of narrowband spectra at block 502 preferably allows the user or process to choose how many narrowband spectra are used and the spectral band of each narrowband spectra. Generally, the number of narrowband spectra employed is able to vary from two to a large number in order to build a desired multi-spectral or hyperspectral data cube. In some implementations, the number of different narrowband spectra used for illuminating the interspersed frames is greater than 10. As an example of an analysis involving only a few narrow band spectra, if spectral analysis is desired only to determine tissue perfusion, the narrowband illuminated frames may only require two series of frames with illumination at 660 nm and 930 nm, respectively, the other frames being illuminated with broad-band white light. In some implementations, the number of different narrowband spectra used for illuminating the interspersed frames may be much higher, such as greater than 50, such larger collections are particularly useful for generating a HSI data cube for later analysis.

Preferably, the process includes selecting narrowband spectra that are interspersed such that the majority of frames are illuminated by white light. For example, in some implementations at least 90% of the frames are illuminated by white light. The selection of narrowband spectra may also include ability to select the spectral bandwidth of the narrowband spectra. For light sources that provide a selectable bandwidth for each of the narrowband spectra, the bandwidth may be selectable for each narrowband spectra individually or for the entire set of narrowband spectra employed. In some embodiments, the system provides ability to select and configure narrowband spectra bandwidth in 5 nm increments starting at a 5 nm bandwidth. For example, in some implementations the process selects a spectral bandwidth of the narrowband illumination spectra of about 5 nm, in other implementations the process selects a spectral bandwidth of the narrowband illumination spectra of about 10 nm, and in other implementations the process selects the spectral bandwidth of the narrowband illumination spectra to be 25 nm. By "about" it is meant that the spectra sizes may vary by several percent, especially depending on how the size is measured, for example the 10 dB bandwidth or other commonly used measures. In some embodiments, at least some of the narrowband spectra overlap with portions of the white light illumination spectrum.

The selection of frame rate for each of the narrowband spectra selects a configuration for how often a narrowband illuminated frame for each particular narrowband spectra is interspersed within the white light frame stream and is preferably at a rate producing an integer multiple of the frame period used for white light illumination such that the narrowband frames fit in the sequence of white light frames, although it should be noted that it is not necessary that the rate of interspersed narrowband illuminated frames occur at a constant interval.

The process provides ability to select the intensity of the white light illumination and the narrowband illumination. Preferably, the intensity of each is selected such that the white light illumination and narrowband illumination have total power that is similarly sufficient such that the exposure characteristics of the sensor do not have to be different for the frames illuminated with narrowband illumination than it is for the frames illuminated by white light in order to acquire data for the multispectral or hyperspectral data cube.

At block 504, the process includes configuring the light source 18 to produce the illumination sequence desired, such as that of FIG. 2 with four different narrowband spectra frames being interspersed in the white light illuminated frames. The selections made at block 502 are configured for at the light source at block 504. For embodiments having a controller at the light source which is able to implement a desired illumination sequence, the configuration at block 504 includes loading the illumination sequence to the light source, or selecting an illumination sequence stored at the light source. For embodiments in which the light source does not have capability to control an illumination sequence itself, the process at block 504 includes loading the selected illumination sequence at a processor connected to the light source, such as CCU 42 (FIG. 6), which then sends commands to the light source to implement the illumination sequence.

At block 506, the process includes operating the light source to intersperse narrowband frame illumination in the white light illumination, for example as shown in FIG. 2. In preferred embodiments, the illumination is directed from a light emitting element of a medical scope to illuminate a subject scene as described herein. The operation may be conducted under control of an electronic processor integrated at the light source, or under control of a camera control unit. During this operation, the light source provides white light illumination at a first frame rate suitable for live video and interrupts the white light illumination to provide narrowband illumination for individual frames interspersed among the white light illuminated frames. The interruption may be at regular or irregular intervals. Generally, the spectrum of the narrowband illumination follows the selected illumination sequence to vary the spectrum of narrowband illuminated frames amongst the interspersed frames sufficient for a series of at least two differently illuminated narrowband interspersed frames to be assembled into a multispectral or hyperspectral data cube at a second frame rate.

At block 508, the process acquires all of the illuminated frames in the sequence, using a scope such as an endoscope. The image light is focused with an optical assembly and directed to a focal plane array sensor of the scope camera, such as image sensor 222 (FIG. 6).

Image frames acquired at the sensor are processed differently depending on whether they are white light illuminated frames or narrowband illuminated frames. Generally, an image signal based on the data acquired at the image sensor is sent to a processor at block 508, which processes the white light illuminated frames as shown in blocks 510, 512, 514, and 516, and processes the narrowband illuminated frames as shown in blocks 511, 513, 515, 517.

For the white light illuminated frames, the process creates a live video feed based on the white light illuminated frames by replacing the narrowband illuminated frames with frames generated from one or more time-adjacent white light illuminated frames. At block 510, the process generates the missing frames, that is the frames to go in place of the narrowband illuminated frames, using a frame repeater to repeat the prior frame adjacent in time to the missing frame, or by using a frame interpolator to create a new frame based on a prior and subsequent frame. At block 512, the process performs image processing such as filtering, enhancement, balancing, and other known image processing functions to prepare the image stream for display and storage. At block 514, the process generates a video feed for the white light illuminated frames, typically at a frame rate equal to the acquisition frame rate of the sensor or the display rate of the monitor, which is set to the overall illumination frame rate (for example, the frame rate of frames 1, 2, and 3 in FIG. 2). Then at block 516, the process prepares and transmits a video encoded signal for display on a first display or a first display area such as first display area 522 illustrated on display 520.

For the narrowband illuminated frames, the process at block 511 assembles the data from the frames into a multispectral or hyperspectral data cube. The data of each narrowband illuminated frame is used for a single "layer" or spectral band of the data cube. For example, in FIG. 2 four different narrowband spectra are used to acquire frames "narrow spectrum frame #1", "narrow spectrum frame #2", "narrow spectrum frame #3", and "narrow spectrum frame #4", which provide the data to populate a 4-layer multispectral data cube providing spectral image data having the image resolution of the focal plane array image sensor. The multispectral or hyperspectral data cube is generated at a second frame rate based on the narrowband illuminated frames, typically at a rate at which the entire sequence of narrowband illuminated frames is repeated in total. For example, in FIG. 2 if a total of four narrowband spectra are used and interspersed with the white light illuminated frames every four frames as depicted, the frame rate for the hyperspectral data cube might be 1/16th of the white light video frame rate. In some embodiments, multiple frames of narrowband illuminated frame data from each narrowband spectra are averaged to fill the multispectral or hyperspectral data cube, in order to eliminate noise. In such case, the frame rate of multispectral or hyperspectral data cube may be reduced to the rate at which the multiple frames of narrowband illuminated frame data are accumulated from the frames acquired at the sensor.

At block 513, the multispectral or hyperspectral data cube is used to perform spectral analysis to identify features of interest and other characteristics, as known in the field of multispectral or hyperspectral imaging analysis. The specific algorithms and techniques used for spectral analysis will vary depending on the application and the number of narrowband spectra employed.

At block 515, the process generates one or more image feeds from information contained in the hyperspectral or multispectral data cube. Then at block 517, the process causes the images to be displayed in separate video feeds on separate display areas than display area 522 showing the white light video feed. In this example, three image feeds are shown to present spectral data showing oxygenation (524), a tissue water index (526) representing tissue water concentration, and a near-infrared (NIR) perfusion index (528) representing perfusion of the tissue in an image scene. These displayed image feeds are preferably updated at the frame rate of the multispectral or hyperspectral data cube as discussed above. While a single display 520 is shown with different display areas presenting the different image feeds, different displays may also be used, or a combination of displays showing one or more of the video or display feeds 522, 524, 526, and 528.

The spectral image video feeds are typically prepared with images colored in a format to match accepted diagnostic techniques, based on the spectral analysis performed at block 513. As such, the spectral analysis at block 513 may be used to map the intensity detected at one or more of the spectra to a specific color on the displayed image, for example. In other spectral imaging techniques, results of other types of spectral analysis may be performed to display data based on the multispectral or hyperspectral data cube in various formats.

FIG. 6 shows a block diagram of system including a light source and an endoscope device for performing spectral analysis as described above. The depicted system is one example of a suitable for performing the process described above.

Figure 1:
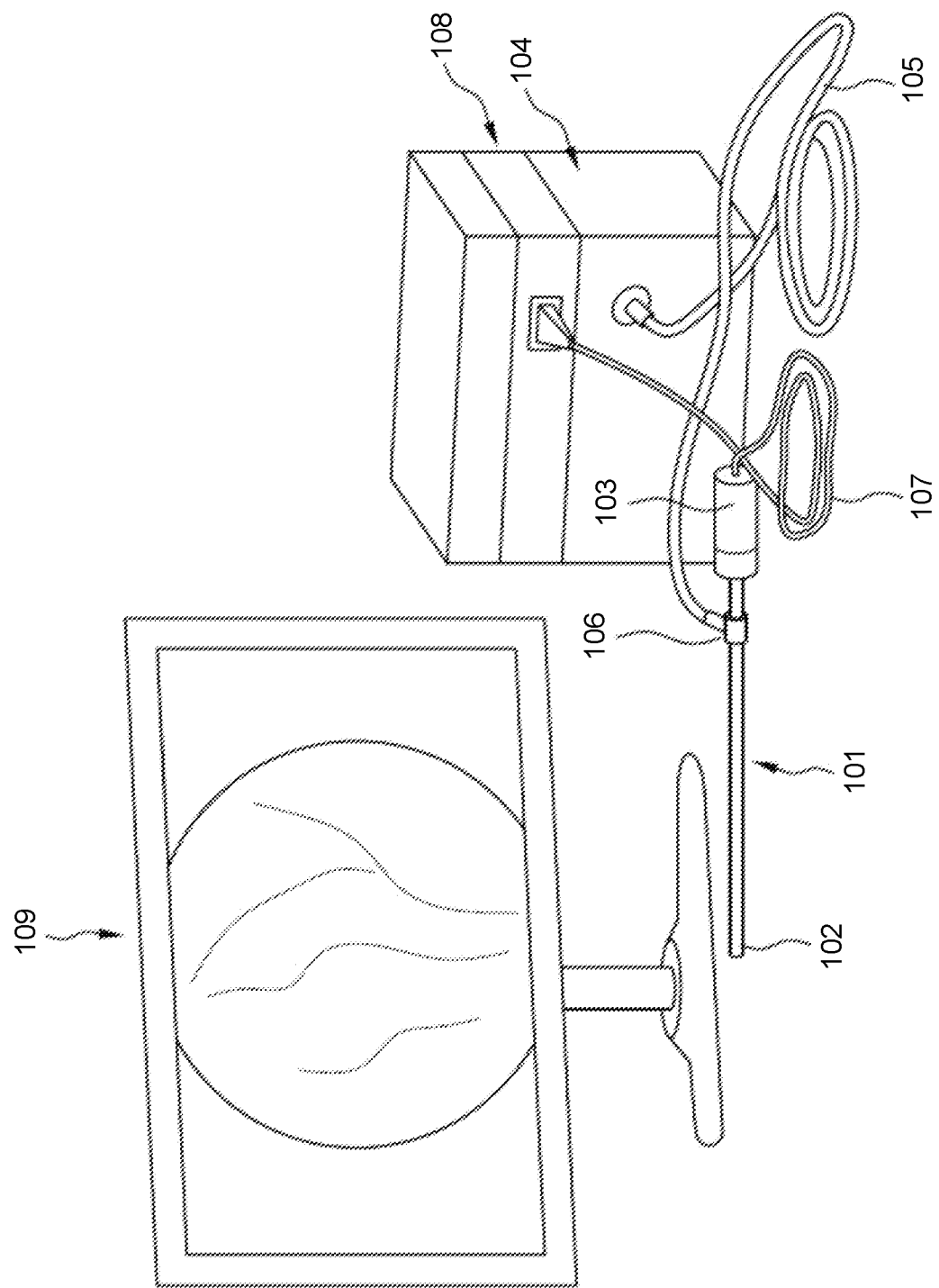
FIG. 1 illustrates a conventional endoscopic imaging system including an endoscope connected by a light guide to an illumination source.

As shown in the diagram of an endoscope device system, a light source 18 illuminates subject scene 19 with visible light and light in multiple narrowband spectra, interspersed as described herein. Light source 18 may be integrated with an endoscope device, or a separate light source providing light to a light post of an endoscope, like that of FIG. 1. Light source 18 may include multiple light emitting elements which are activated and deactivated to provide the white light and narrowband light in each narrowband spectrum employed, or light source 18 may include a broad spectrum light emitting element and an optical assembly for spectrally isolating desired narrowband spectra and directing them toward the subject scene in the desired sequence. For example, light source 18 may include a broad spectrum light source, a spectral dispersion element such as a prism or diffraction grating positioned to disperse the light spectrally, and a spatially selective element such as a digital light projection (DLP) mirror array for directing the desired narrowband illumination toward subject scene 19. Such a light source is the OL490 Agile Light Source produced by OPTE-E-MA Engineering GmbH (Martinroda, Germany). Further, light source 18 may include fiber optics passing through the body of the scope, or other light emitting arrangements such as LEDs or laser diodes positioned at or near the front of the scope.

As shown in the drawing, light 20 reflected from the subject scene is input to an optical assembly 21, where the light is focused to form an image at a solid-state image sensor 222.

Optical assembly 21 includes an optical relay system of an endoscope or other medical scope. An additional lens group may be included at the camera head. As discussed above, portions of the optical assembly may be embodied in a camera head or other first optical device, while other portions are in an endoscope or other scope device, or the optical assembly 21 may be contained in a single imaging device. Image sensor 222 (which may include separate R, G, and B sensor arrays) converts the incident light to an electrical signal by integrating charge for each picture element (pixel). The image sensor 222 may be active pixel complementary metal oxide semiconductor sensor (CMOS APS) or a charge-coupled device (CCD).

The total amount of light 20 reaching the image sensor 222 is regulated by the light source 18 intensity, the optical assembly 21 aperture, and the exposure of a given collected frame is based on the amount of light reaching the image sensor 222 and the time for which the image sensor 222 integrates charge. Exposure/sequence controller 40 responds to the amount of light available in the scene given the intensity and spatial distribution of digitized signals corresponding to the intensity and spatial distribution of the light focused on image sensor 222. In some embodiments, exposure/sequence controller 40 also controls the timing and intensity of white light illumination and narrowband illumination from light source 18, in order to produce the narrowband illuminated frames as discussed above. In other embodiments, light source 18 includes a controller which performs the sequencing function of exposure/sequence controller 40 onboard the light source and may be configurable through user interface 60 over a serial connection from system controller 50 to light source 18 to configure the spectrum, intensity, and timing and sequence of illumination needed to produce the white light illuminated frames and narrowband illuminated frames as discussed above. Exposure/sequence controller 40 may also control the optical assembly 21 aperture, and indirectly, the time for which the image sensor 222 integrates charge. The control connection from exposure/sequence controller 40 to timing generator 26 is shown as a dotted line because the control is typically indirect.

Analog signals from the image sensor 222 are processed by analog signal processor 22 and applied to analog-to-digital (A/D) converter 24 for digitizing the analog sensor signals. The digitized signals each representing streams of image frames or image representations based on the data, are fed to image processing circuitry 30 as image signal 27.

Image processing circuitry 30 performing digital image processing functions to process and filter the received images as is known in the art. Image processing circuitry may include separate, parallel pipelines for processing the white light illuminated frames and narrowband illuminated frames separately. Image processing circuitry 30 and system controller 50 may perform autofocus algorithms to make focal adjustments based either white light imaging or fluorescence imaging.

Spectrographic analysis circuitry 32 receives the partial spectrograph images and performs spectrographic analysis including normalizing the data based on the spectral transfer function of the spectrometer optics, calculating spectral content, and creating a combined image spectral data set including spectral data from each of the narrowband illuminated frames. Such a data set is referred to as a multispectral or hyperspectral data cube but may be stored in a variety of data structures in various embodiments. Spectrographic analysis circuitry 32 may also perform spectral analysis to identify, classify, or highlight features found in the image spectral data set, and prepare representative images for display to visualize or otherwise present the spectrographic data in the spectral data set. As such, spectrographic analysis circuitry 32 may perform any suitable processing and visualization techniques employed with multispectral imaging (MSI) and hyperspectral imaging (HSI) analysis.

Timing generator 26 produces various clocking signals to select rows and pixels and synchronizes the operation of image sensor 222, analog signal processor 22, and A/D converter 24. Image sensor assembly 28 includes the image sensor 222, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure/sequence controller 40 to set the light source 18 intensity, spectral output, the optical assembly 21 aperture, and controlling various filters in optical assembly 21 and timing that may be necessary to obtain image streams based on the visible light. In some versions, optical assembly 21 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 68. This display is typically a liquid crystal display backlit with light-emitting diodes (LED LCD), although other types of displays are used as well. The processed image data can also be stored in system memory 56 or other internal or external memory device.

The user interface 60, including all or any combination of image display 68, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g., on image display 68). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Such settings may include different settings for different models of scopes that may be attached to a camera head or other imaging device containing image sensor assembly 28.

Image processing circuitry 30 and spectrographic analysis circuitry 32 are embodied together in one of three programmable logic devices, processors, or controllers in this embodiment, in addition to a system controller 50 and the exposure/sequence controller 40. Image processing circuitry 30, controller 50, exposure/sequence controller 40, system and program memories 56 and 54, video encoder 80 and display controller 82 may be housed within camera control unit (CCU) 42.

CCU 42 may be responsible for powering and controlling light source 18, image sensor assembly 28, and/or optical assembly 21. In some versions, a separate front end camera module may perform some of the image processing functions of image processing circuitry 30.

Image processing circuitry 30, spectrographic analysis circuitry 32, system controller 50, system and program memories 56 and 54, video encoder 80, and display controller 82 may be housed within camera control unit (CCU) 42. CCU 42 may be responsible for powering and controlling light source 18 and/or image sensor assembly 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An endoscopic video system comprising:
   a light source adapted to provide white light illumination at a first frame rate suitable for live video, and to interrupt the white light illumination and provide narrowband illumination for individual frames interspersed among the white light illuminated frames at regular or irregular intervals, wherein the spectrum of the narrowband illumination varies amongst the interspersed frames sufficient for a series of at least two differently illuminated narrowband interspersed frames to be assembled into a multispectral or hyperspectral data cube at a second frame rate; and
   a processor adapted to receive an image signal based on sensor data received from a focal plane array sensor and create a live video feed based on the white light illuminated frames by replacing the narrowband illuminated frames with frames generated from one or more time-adjacent white light illuminated frames, and to generate the multispectral or hyperspectral data cube at a second frame rate based on the narrowband illuminated frames.

2. The system according to claim 1 the majority of frames are illuminated by white light.

3. The system according to claim 2 wherein at least 90% of the frames are illuminated by white light.

4. The system according to claim 1 wherein at least some of the narrowband spectra overlap with portions of the white light illumination spectrum.

5. The system according to claim 1 wherein the number of different narrowband spectra used for illuminating the interspersed frames is greater than 10.

6. The system according to claim 1 wherein the number of different narrowband spectra used for illuminating the interspersed frames is greater than 50.

7. The system according to claim 1 wherein the processor is further adapted to generate an image from information contained in the hyperspectral or multispectral data cube and cause the image to be displayed in a separate display area than a display area showing the video feed.

8. The system according to claim 7 wherein the image generated from the hyperspectral data cube indicates the oxygenation, tissue water index, or perfusion of tissue in an image scene.

9. The system according to claim 1 wherein the spectral bandwidth of the narrowband illumination spectra is about 5 nm.

10. The system according to claim 1 wherein the spectral bandwidth of the narrowband illumination spectra is about 10 nm.

11. The system according to claim 1 wherein the spectral bandwidth of the narrowband illumination spectra is about 25 nm.

12. The system according to claim 1 wherein the white light illumination and the narrowband illumination have total power that is similar sufficient such that exposure characteristics of the sensor do not have to be different for the frames illuminated with narrowband illumination than it is for the frames illuminated by white light in order to acquire data for the multispectral or hyperspectral data cube.

13. The system according to claim 1 wherein data from multiple narrowband illuminated frames of identical narrowband illumination are averaged to generate a data cube and/or a slice of a data cube.

14. A method comprising:

causing a light source for a medical scope to provide white light illumination for frames at a first frame rate suitable for live video;

causing the light source to interrupt the white light illumination and provide narrowband illumination for individual frames interspersed among the white light illuminated frames at regular or irregular intervals, wherein the narrowband spectrum varies amongst the interspersed frames sufficient for a series of at least two differently illuminated narrowband interspersed frames to be assembled into a multispectral or hyperspectral data cube at a second frame rate;

imaging the white light illuminated fames and narrowband illuminated frames onto a focal plane array image sensor at the medical scope;

at a processor, receiving an image signal based on sensor data received from the focal plane array sensor and creating a live video feed based on the white light illuminated frames by replacing the narrowband illuminated frames with frames generated from one or more time-adjacent white light illuminated frames; and at the processor, generating a multispectral or hyperspectral data cube at a second frame rate based on the narrowband illuminated frames.

15. The method according to claim 14 further comprising generating an image from information contained in the hyperspectral or multispectral data cube and displaying said image on a separate display area than the live video feed.

16. The method according to claim 15 wherein the image generated from the hyperspectral data cube indicates the oxygenation, tissue water index, or perfusion of tissue in an image scene.

17. The method according to claim 14 wherein the spectral bandwidth of the narrowband illumination spectra is about 5 nm.

18. The method according to claim 14 wherein the spectral bandwidth of the narrowband illumination spectra is about 10 nm.

19. The method according to claim 14 wherein the spectral bandwidth of the narrowband illumination spectra is about 25 nm.

20. The method according to claim 14 wherein the white light illumination and the narrowband illumination have total power that is similar sufficient such that exposure characteristics of the sensor do not have to be different for the frames illuminated with narrowband illumination than it is for the frames illuminated by white light in order to acquire data for the multispectral or hyperspectral data cube.

* * * * *